US006414123B1

(12) United States Patent
Musick et al.

(10) Patent No.: US 6,414,123 B1
(45) Date of Patent: *Jul. 2, 2002

(54) METHOD FOR PURIFYING FSH

(75) Inventors: James R. Musick, Conifer; Erik Van Horn, Denver, both of CO (US)

(73) Assignee: Vitro Diagnostics, Inc., Littleton, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,132

(22) Filed: Nov. 16, 1999

Related U.S. Application Data

(63) Continuation-in-part of application No. 09/075,423, filed on May 8, 1998, now Pat. No. 5,990,288.
(60) Provisional application No. 60/065,405, filed on Oct. 21, 1997.

(51) Int. Cl.$^7$ .............................. C07K 3/18; C07K 3/20; C07K 3/28
(52) U.S. Cl. ...................... 530/398; 530/397; 530/344; 530/350; 530/412; 530/413; 530/415
(58) Field of Search ................................. 530/344, 397, 530/398, 350, 412, 413, 415

(56) References Cited

U.S. PATENT DOCUMENTS

| | | | |
|---|---|---|---|
| 3,973,004 A | | 8/1976 | Volynsky et al. ............ 530/399 |
| 4,404,188 A | | 9/1983 | Donahoe et al. |
| 5,128,453 A | | 7/1992 | Arpala et al. ................ 530/398 |
| 5,338,835 A | * | 8/1994 | Boime ......................... 530/398 |
| 5,338,855 A | * | 8/1994 | Yoshioka ..................... 514/369 |
| 5,744,587 A | | 4/1998 | Alaska et al. ................ 424/108 |
| 5,990,288 A | | 11/1999 | Musick et al. ............... 530/398 |

FOREIGN PATENT DOCUMENTS

| | | |
|---|---|---|
| GB | 1069945 | 7/1965 |
| WO | 98 20039 | 5/1998 |
| WO | 00 04913 | 2/2000 |

OTHER PUBLICATIONS

Govoroun, M.S., et al, "Use of immobilized metal ion affinity chromatography and dye ligand chromatography for the separation and purification of rainbow trout pituitary gonadotropins, GTH I and GTH II," Journal of Chromatography, vol. 698, No. 1–2, pp. 35–46 (1997).

Moore, L.G., et al, "Follicle–Stimulating Hormone in the Brushtail Possum (*Trichosurus vulpecula*): Purification, Characterization, and Radioimmunoassay," Gen. Comp. Endo., 106, pp. 30–38 (1997).

Subramanian, S., "Dye–Ligand Affinity Chromatography: The Interaction of Cibacron Blue F3GA With Proteins and Enzymes," Critical Reviews in Biochemistry, vol. 16, No. 2, pp. 169–205 (1984).

* cited by examiner

*Primary Examiner*—Christopher S. F. Low
*Assistant Examiner*—Abdel A. Mohamed
(74) *Attorney, Agent, or Firm*—Susan T. Hubl; Quine Intellectual Property Law Group, P.C.

(57) ABSTRACT

The present invention provides a method for purifying follicle stimulating hormone (FSH) from biological samples, for example, from human pituitary glands or human postmenopausal urine, wherein the FSH is contaminated with other proteins, by use of dye-ligand affinity chromatography (DAC). Depending on the starting material used and the initial purity of FSH in the starting material, additional purification steps may be employed. These steps preferably involve the use of hydrophobic interaction chromatography. This process may be used to generate affinity pure FSH suitable for therapeutic applications. The methods of the invention provide high purity FSH with high overall yield. A further advantage is the ability to easily regenerate the chromatography media for re-use, thus providing added economy to the purification process.

12 Claims, No Drawings

METHOD FOR PURIFYING FSH

CROSS REFERENCES TO RELATED APPLICATIONS

This application is a continuation-in-part of application Ser. No. 09/075,423, filed May 8, 1998, now U.S. Pat. No. 5,990,288, which claims the benefit of U.S. Provisional Application No. 60/065,405, filed Oct. 21, 1997.

TECHNICAL FIELD

The present invention relates to the protein purification arts and more specifically to methods for producing highly purified follicle stimulating hormone (FSH) to high purity FSH compositions.

BACKGROUND OF THE INVENTION

Follicle stimulating hormone (FSH, or follitropin) is a pituitary heterodimeric glycoprotein hormone synthesized and released from gonadotrope cells of the anterior pituitary gland. As a circulating hormone, FSH interacts with high affinity with receptor molecules on the surface of granulosa cells in the ovary. This interaction evokes a series of intracellular events, including increasing intracellular levels of the second messenger, cyclic AMP, and elicitation of a steroidogenic response by the granulosa cells resulting in estrogen production. Local estrogen and FSH stimulation promote the growth and maturation of ovarian follicles.

The amount of circulating FSH is dependent upon several other endocrine and neural factors. Gonadotropin releasing hormone (GnRH) is a peptide elaborated by hypothalamic neurons. Released GnRH interacts with receptors on pituitary gonadotrope cells to control the synthesis and release of FSH and leutenizing hormone (LH) from the anterior pituitary gland. FSH secretion also is affected by circulating levels of steroid hormones. The steroidogenic response of granulosa cells to FSH results in gradually increasing estradiol levels. When serum estradiol reaches a critical level, it triggers a large increase in the rate of LH and FSH release from the anterior pituitary. The resultant LH surge induces ovulation and luteinization of granulosa cells. Progesterone is released from the corpus luteum following ovulation and this steroid prepares the uterus for implantation of the fertilized ovum. Elevated levels of estrogens and progesterone exert a negative feedback inhibition at hypothalamic sites to lower FSH and LH synthesis and release. Hence, the effects of steroids on gonadotropin release depend on the circulating levels; at low levels of estrogen, FSH and LH are positively regulated while higher levels result in negative feedback inhibition.

In males, FSH induces spermatogenesis through a proliferative effect on spermatocytes. Sperm production also requires testosterone, which is under positive regulatory control by LH.

An apparent paradox of the above-described hormonal control process is the production of both LH and FSH by the gonadotrope cell while GnRH serves as a positive regulatory agent for both hormones. Work within the last 10 years suggests that the peptides activin, follistatin, art and inhibin selectively regulate FSH secretion from the anterior pituitary gland. FSH synthesis and release are activated by activin, while inhibin and follistatin have negative feedback effects. The inhibitory effect of follistatin is thought to be mediated by its high-affinity binding to activin and blockage of its biological activity. There is evidence for both autocrine and paracrine local regulatory effects of these peptides and for feedback effects of inhibin released from gonadal tissue. Both inhibin and activin are structurally related and are members of the diverse transforming growth factor beta family of peptides. Study of the physiological roles of activin, follistatin, and inhibin is a current area of active research (reviewed by Knight, 1996).

FSH has been used extensively as a drug to treat human infertility by induction of follicular development in females. Earlier products were crude preparations of LH and FSH, i.e., Pergonal®. More recently developed products contain purer FSH preparations. Metrodin® has low levels of LH and the FSH specific activity is about 100 IU of FSH per mg total protein. This drug requires intramuscular injections every day for 5 to 7 days, followed by a single injection of human chorionic gonadotropin (hCG) to induce ovulation. A recent advance is Fertinex® which is affinity-purified FSH from human menopausal gonadotrophin (hMG). This product exhibits a FSH potency of 8500 to 13,500 IU of FSH per mg total protein at 95% purity as reported by the manufacturer. The high purity of Fertinex® allows delivery by subcutaneous injection, which can be administered at home. Following administration of Fertinex®, hCG is used for induction of ovulation. Depending on the dosage of FSH administered, it may be used to promote in vivo fertility or, at higher dosages, it may be used to induce multiple oocyte formation for in vitro fertilization procedures. Recombinant forms of FSH (Puregon® and Gonal®) also are used as fertility drugs; these versions of FSH have potencies and-purities similar to that of Fertinex®.

FSH has been purified from pituitary glands, human postmenopausal urine, and from culture media collected from genetically engineered cells. FSH purification has been an active area of research over the past 30 years. Older methods rely on procedures such as ion exchange chromatography, size exclusion chromatography, polyacrylamide gel electrophoresis, and chromatography on hydroxylapatite. In one method (Roos, et al., 1968) a FSH preparation of 14,000 IU of FSH per mg total protein was obtained from fresh frozen human pituitary glands with an overall recovery of activity of 5.0%. A similar procedure applied to urinary FSH resulted in a preparation of 780 IU of FSH per mg total protein at a 7.7% overall yield.

Because of the similar physicochemical properties of FSH and LH, i.e., similar molecular weight and overlapping isoelectric profiles, affinity chromatography methods have been employed to improve the separation of LH from FSH. Affinity methods also afford the possibility of high purification in a single step (up to 100-fold) thereby reducing the number of steps in a purification method and improving overall yield. The latter is a critical factor in the commercial production of FSH as overall yield is a major determinant of cost. Group-specific affinity adsorbents such as the lectin Concanavalin A or chitosan (Japanese patent number 8,027, 181) bind glycoproteins via specific carbohydrate groups. Concanavalin A has been used to characterize microheterogeneity of purified FSH preparations (Chapped, et al., 1983). However, these ligands are ineffective in the separation of two glycoproteins such as FSH and LH.

Immunoaffinity chromatography (IAC) relies upon the specificity of mono- or polyclonal antibodies for capture of specific protein antigens from crude mixtures. Antibodies may first be screened for use in IAC (Bonde, et al., 1991). The selected antibodies are coupled to a chromatographic solid phase, e.g., cross-linked agarose, through covalent bonds, e.g., cyanogen bromide (CNBr) or other coupling chemistries targeting surface amino, hydroxyl, carboxyl or sulfhydryl groups of immunoglobulins to form a solid matrix. Recent coupling methods attempt site-directed immobilization of antibodies in an effort to optimize antigen-binding efficiencies, which are typically low, using classical coupling chemistries. One method of site-directed coupling is through carbohydrate groups of the $F_c$ immunoglobulin region to hydrazide-activated solid supports (Hoffman and O'Shannessy, 1988). The solid phase coupled to antibody then is packed in a chromatography column and equilibrated with buffer for binding to antigen. Mixtures of target protein and contaminants are equilibrated with binding buffer and then applied to the column. Non-adsorbed contaminants are removed by washout with various buffers. Elution occurs by use of chaotropic agents, extremes of pH, changes in ionic strength, etc.. Elution is a critical aspect of IAC since the elution conditions may alter the biological activity of the immobilized antibody or the eluted antigen or both (reviewed by Jack, 1994).

IAC may be used to remove specific contaminants from a crude mixture. This mode first was applied to FSH purification using antibodies to hCG, which through cross reactivity to LH, effectively reduced LH contamination levels (Donini, et al., 1966). Other methods (Jack, et al., 1987 and Great Britain patent number 8,510,177) utilized monoclonal antibody specific to FSH for IAC. The antibody was coupled to CNBr-activated Sepharose 4B. Samples were applied in a buffer of 0.05 M borate, 0.5 M NaCl at pH 8.5 and non-adsorbed contaminants were eluted from the column with 0.05 M borate at pH 8.5. The bound FSH was eluted using 0.1 M glycine, 0.5 M NaCl at pH 3.5. When using a sample containing the glycoprotein-enriched fraction from a side-fraction of human growth hormone obtained from frozen pituitaries, 47% of the applied FSH was recovered from the IAC procedure. The FSH was recovered at a specific activity of 10,000 IU of FSH per mg total protein. It contained 0.0014 IU of LH per IU of FSH and thyroid stimulating hormones (TSH) at 0.93 $\mu$IU of TSH per IU of FSH (Jack, et al., 1987). Another IAC method for FSH relies on a monoclonal antibody to FSH that is coupled to Sepharose 4B by divinylsulphone (U.S. Pat. No. 5,128,453). The column and sample were equilibrated with 0.1 M Tris, 0.3 M NaCl at pH 7.5 and the IAC procedure was performed at 4° C. In this case, partially purified urinary FSH (hMG) was used as a sample. The sample was applied in the equilibration buffer and nonadsorbed materials were removed by continued washing with this buffer. FSH elution was accomplished by use of high ionic strength alkaline buffers, e.g., 1 M ammonia or other eluents of pH>11 and of ionic strength greater than 0.8 M. The product of IAC was then subject to reverse phase HPLC on a C18 column to generate the final product. While the yield of FSH activity from the IAC step was not given, the final product had a specific biological activity of 6200 IU of FSH per mg total protein (specific biological activity=1.2×specific immunological activity for this purified material) and had undetectable levels of LH contamination by radio immunoassay (RIA) measurement. No other protein contaminants were detected by SDS-PAGE analysis.

Other researchers have recently reported the use of dye affinity chromatography (DAC) in the purification of FSH from the brushtail possum. Their purification involved several steps including the use of Green A Matrix gel and Red A Matrix gel (Amicon, Inc., Beverly, Mass.) for two sequential DAC procedures. The overall yield of their method was 12% (Moore, et al., 1997).

SUMMARY OF THE INVENTION

The present invention provides a process for the purification of FSH by use of DAC. The method utilizes a dye ligand, for example an orange dye ligand, preferably Orange 1 (Prometic Biosciences, Inc., Burtonsville, Md.), which is coupled to cross-linked agarose via triazine coupling chemistry to form a solid matrix. Other dye ligands also may be used, for example, Orange 2, Yellow 2 or Green 1 (Prometic Biosciences, Inc., Burtonsville, Md.). Orange 1 shows strong selectivity to FSH when the binding occurs at low ionic strength and acidic pH, for example, about pH 4.0. Samples containing FSH and excess amounts of LH fail to exhibit significant LH binding under these conditions and LH contamination is conveniently removed by elution with an appropriate washout buffer. FSH then may be eluted from the dye by increasing eluent ionic strength, for example, by use of a linear salt gradient, preferably 0 to 0.6 M NaCl. Alternatively, eluent ionic strength can be increased stepwise to elute the FSH. Other means of eluting or releasing the bound FSH may be used such as, for example, increasing pH or using agents which compete for FSH binding to the dye ligand. The result is FSH product containing only minimal contamination by LH and other unwanted proteins. Residual contamination of FSH by LH and other unwanted proteins may then be removed by, for example, hydrophobic interaction chromatography (HIC) or ion exchange chromatography. The FSH purification methods of the present invention have been used to purify, for example, human pituitary FSH, human urinary FSH, human recombinant FSH, human FSH secreted from gonadotropes, and bovine FSH. The present method may also be used to purify FSH from other species, particularly mammalian, including, for example, equine, porcine, ovine, canine, feline, rat, mouse and monkey.

The present invention operates at high yields (>95% recovery of FSH activity) and with high purification factors (up to about 50-fold) depending upon the sample used. The method is non-denaturing to FSH and this allows for high overall recoveries in multi-step purification procedures as needed, for example, when FSH is purified from human pituitary glands. Also, the ligand shows minimal ligand leakage and can be regenerated with substantially complete restoration of FSH binding properties. Therefore, the dye may be used for at least 25 cycles prior to loss of effective binding and release of FSH.

The advances of this invention over the prior art include the advantages of affinity chromatography by DAC as compared to IAC. The primary advance is in the ease of elution of bound FSH from the immobilized dye ligand as compared to an immobilized antibody. While very gentle elution conditions are used in the present invention, e.g., sodium chloride gradient at pH 6.0, elution from an IAC column usually involves relatively harsh conditions. One IAC method involves use of an elution buffer at pH 3.5 to elute bound FSH (Jack et al., 1987). This pH has deleterious effects on the immunological activity of human FSH. While use of alkaline pH (U.S. Pat. No. 5,128,453) eliminates the harmful effects of low pH, the effects of alkaline pH on the immobilized antibody are unknown. Even minor effects on the immobilized antibody could tend to decrease the effectiveness of the immunoadsorbant with continued use cycles. In addition, IAC requires highly consistent batches of monoclonal antibody and coupling procedures, which may result in low antigen binding efficiencies. Lower binding capacity would require larger amounts of antibody to bind a given amount of antigen. DAC relies on an inert ligand, which can be manufactured and coupled in a highly reproducible manner.

Another advantage of DAC resins is in sanitization. DAC resins may by sanitized and depyrogenated by treatment with 1.0 N NaOH without effect on chromatographic performance. Such treatment of IAC resins usually results in inactivation of the antibody. Therefore, sanitation of IAC resins is more difficult to achieve. Minimal ligand leakage from DAC resins also results in lower product contamination, while antibody leakage from IAC resins can contaminate the product. For reviews of DAC see: Lowe, et al., (1992) and Garg, et al., (1996).

DETAILED DESCRIPTION OF PREFERRED EMBODIMENTS

This invention is intended for use with biological materials, particularly relatively crude mixtures of FSH, LH and other contaminating proteins referred to herein as starting material sample(s) or starting material(s) or sample(s). The examples described in detail below use starting material samples obtained during pituitary hormone purification from human or bovine pituitary glands; hMG prepared from human menopausal urine; FSH derived from primary cultured human gonadotrope cells; and crude preparations of recombinantly produced human FSH (recombinant human FSH). Alternative sources of starting material might include: 1) FSH extracted from the pituitary glands obtained from other species, especially mammalian, for example, equine, porcine, ovine, canine, feline, rat, mouse, and monkey; 2) recombinant FSH or FSH derived from the gonadotropes or gonadotrope cell lines obtained from other species, especially mammalian, for example, bovine, equine, porcine, ovine, canine, feline, rat, mouse, and monkey; 3) genetically or otherwise altered forms of FSH (Szkudlinski, et al., 1996; U.S. Pat. No. 5,338,835) obtained from various species, especially mammalian, for example, human, bovine, equine, porcine, ovine, canine, feline, rat, mouse, and monkey. In any case, the sample is substantially free of TSH, prolactin, and growth hormone and the FSH comprises about 2–5% of the sample. The LH contamination varies according to the sample but may be as high as 200%.

The sample can be prepared for DAC by standard methods of sample preparation including concentration-diafiltration or concentration and desalting using size exclusion chromatography. The sample preferably is equilibrated with sodium acetate with or without leupeptin as a protease inhibitor. More preferably, the sample is equilibrated with about 1 mM to about 5 mM sodium acetate containing about 1 $\mu$M to about 2 $\mu$M leupeptin at pH 4.0 to 5.5. Even more preferably, the sample is equilibrated with 5 mM sodium acetate at pH 4.0. For longer term storage of these samples, it is preferable to use 1 mM to 5 mM Tris-acetate, more preferably 1 mM, as the equilibration buffer and maintain the sample pH at 7 to 9.5, more preferably pH 9.5. The sample may be stored liquid or frozen in this buffer without appreciable loss of FSH activity. The sample should only be exposed to low pH (e.g., about 4) for relatively short time periods just prior to its application to the DAC column. Longer-term exposure to 5 mM sodium acetate at pH 4.0 can lead to FSH inactivation.

The DAC column is prepared in, preferably, a glass chromatography column of appropriate dimensions for the sample to be used and the target loading volume of the DAC media. In general one of skill in the art will readily determine appropriate volumes of DAC media to use, based on the capacity of the medium to bind FSH. The capacity can be determined by, e.g., incubating aliquots of medium with different volumes of sample, and determining the amount of FSH remaining in the sample. The column is packed with the solid matrix comprising an appropriate dye coupled to the solid phase, preferably Mimetic Orange 1 (Prometic Biosciences, Inc., Burtonsville, Md.; Cat. No. A6XL 0030). The column then is equilibrated with several column volumes, preferably at least 8, of sodium acetate at acidic pH at a linear flow rate of 60–120 cm/hr. Linear flow rate for a cylindrical column is defined as flow rate, expressed as mL/hr, divided by $\pi r^2$ where r equals the column radius in cm. The conductivity of the sample is desirably less than 1 mS prior to binding. The sample is at acidic pH, preferably about 4.0, in either sodium acetate (preferably about 5 mM) or Tris-acetate (preferably about 1 mM). An aliquot of the sample is taken for later assay. The sample is applied to the column, preferably at 30 cm/hr or less. Sample application is followed by application of a sodium acetate buffer, at pH 4.0, for several column volumes at about 60 cm/hr. This is followed by washout of non-adsorbed LH and other proteins using a $NaH_2PO_4$ buffer at pH about 6.0. Washout with this buffer continues for a total of several column volumes at about 60 cm/hr. FSH is then eluted or released by use of a salt buffer which also contains $NaH_2PO_4$ at pH about 6.0. Elution of FSH by use of a salt buffer is done using a linear salt gradient, or alternatively, performed with a step-wise increase in buffer salt concentration. As an alternative to releasing FSH with increasing ionic strength, FSH also can be eluted using increasing pH or agents that compete with FSH binding to the dye ligand.

The following examples are intended to be descriptive of the instant invention and are in no way intended to limit the scope of the invention claimed herein.

EXAMPLE 1

Purification of FSH Human Pituitary Glands

The sample used for FSH purification was derived from a process used for the extraction and purification of LH, FSH, and TSH (Hartree, 1966). The side fraction used for FSH purification was derived from an acid extract (pH 4.0) of 3218 glands that was initially processed through cation exchange chromatography (CIX) on Fractogel EMD $SO_3$-650M (EM Separations Technology, Gibbstown, N.J.). The extract was bound to this resin at pH 4.5 in 0.1 M NaCl, 10 mM sodium acetate. The hormones were eluted by use of a 10 column-volume linear gradient to 0.8 M NaCl, 8 mM sodium acetate, pH 4.5. This step resulted in nearly quantitative recoveries of LH, FSH, and TSH and 5- to 10-fold purification of the hormones. The sample containing TSH, LH, and FSH resulting from CIX was concentrated 10-fold and brought to 1.5 M ammonium sulfate by the addition of solid ammonium sulfate. It then was bound to PAE 1000 L (Amicon, Inc., Beverly, Mass.) using a batch procedure. Following washout with 1.5 M ammonium sulfate, 20 mM sodium acetate, pH 4.5, TSH was separated from LH and FSH by elution with a 15 column-volume decreasing salt gradient to 0.25 M ammonium sulfate, 20 mM sodium acetate, pH 4.5, followed by a step to 20 mM sodium acetate, pH 4.5. This last step was maintained for about 3 column volumes.

The sample prepared as set forth above contained 852,480 IU of FSH, 1,868,130 IU of LH, and 3800 mg of total protein. The activities of FSH and LH present were determined by immunoassay using either the Abbott ImX™ (Fiore, et al., 1988) or Chiron Diagnostics ACS:180™ (Boland, et al., 1990) method standardized to reference preparations of the hormones provided by the World Health Organization. Total protein was determined using the absorbance at 280 nm ($A_{280}$), using a cuvette with a 1 cm path length and assuming that a solution of 1 mg/mL total protein yields 1.00 absorbance units. The initial sample was in a buffer containing 1.25 M ammonium sulfate, 20 mM Tris, 1 $\mu$M leupeptin at pH 8.6. This sample was prepared for chromatography on Orange 1 by concentration from 10.325 L to about 600 mL in a hollow fiber ultrafiltration device (M12 ProFlux™, Amicon, Inc., Beverly, Mass.) equipped with a 10,000 Dalton-cutoff membrane (S10, Y10, Amicon, Inc., Beverly, Mass.). Concentration occurred at a flow rate of 3 L/min with 15 PSI back pressure applied to the hollow fiber cartridge. The sample was then diafiltered with 1 mM Tris-acetate, 1 µM leupeptin at pH 9.5 until the conductivity of the sample was less than 1 mS. The sample was recovered from the M12 device and the hollow fiber cartridge was washed out with 2×300 mL of 1 mM Tris-acetate, 1 µM leupeptin at pH 9.5. These washes were combined with the concentrated sample, which was then was centrifuged at 6300×g for 15 minutes and the volume of the supernatant was measured. The conductivity and $A_{280}$ were determined and a small aliquot was removed for immunoassay. The sample could be stored at 4° C. or −20° C. In this example, its pH was adjusted to 4.0 with acetic acid following preparation of the column as described below. The sample is adjusted to pH 4.0 just prior to its application to the chromatography column.

The chromatography column was glass, 4.4×25 cm (Vantage L, VL 44X250, Amicon, Inc., Beverly, Mass.). It was packed and operated at room temperature. The column was packed with Mimetic Orange 1 (Prometic Biosciences, Inc., Burtonsville, Md.; Cat. No. A6XL 0030) according to the manufacturer's recommendations to a bed volume of 243 mL. The column was operated on a dual pump bio-chromatography system equipped with a computer controlled gradient formation system (two pumps No. 222C with 0–30 mL/min heads; controller model 232D; Scientific Systems, State College, Pa.). It was equilibrated with start buffer (5 mM sodium acetate, 1 µM leupeptin, pH 4.0) at 60 cm/hr. Prior to sample application to the column, the eluate pH was 3.8 to 4.3 and its conductivity was<1.3 mS.

The sample, which had been previously adjusted to pH 4.0 with acetic acid, was then applied to the column at 15 cm/hr. A peristaltic pump was used for sample application. The column was loaded at 15 mg total protein per mL of packed bed volume. The column then was eluted according to a programmed elution regime. The flow rate was 60 cm/hr throughout elution: 10 column volumes with start buffer (5 mM sodium acetate, 1 µM leupeptin, pH 4.0); 10 column volumes with washout buffer (0.025 M $NaH_2PO_4$, 0.02% $NaN_3$, 1 µM leupeptin, pH 6.0); 10 column volume linear gradient from washout buffer to elution buffer (0.025 M $NaH_2PO_4$, 2.0 M NaCl, 1 µM leupeptin, 0.02% $NaN_3$, pH 6.0). The washout buffer was effective in removing unbound LH and other contaminating proteins as well. As an alternative to the linear gradient, the FSH is released from the column using a step-wise increase in ionic strength with 3 column volumes of elution buffer (0.025 M $NaH_2PO_4$, 2.0 M NaCl, 1 µM leupeptin, 0.01% $NaN_3$, pH 6.0). The column eluate was collected by a fraction collector and the fractions were analyzed to determine total protein and FSH and LH immunological activities as described above. The column was stored in 0.1 M NaCl/EtOH (75/25) (v/v). FSH was recovered from the DAC process at relatively high purity (see Table 1). The LH contamination was reduced from 78.3% to 1.3%.

Hydrophobic interaction chromatography may be used to remove residual amounts of LH from FSH. The FSH-containing fractions from the DAC run were eluted during the gradient to elution buffer as a rather broad peak following an earlier, sharper peak containing LH and non-hormone contaminates. This FSH sample was prepared for HIC by first pooling the FSH-containing fractions from the DAC run and then adjusting the sample pH to 8.5 with NaOH. The sample then was concentrated to 1–2 mg/mL FSH using a hollow fiber ultrafiltration device equipped with a 10,000 Dalton cutoff membrane (AG Technologies, Needham, Mass.; Cat. No. UFP-10-E-4A). The sample was diafiltered with 5 to 10 volumes of 1 mM Tris-acetate at pH 8.5. This sample may be stored at 4° C. or −20° C.

The chromatography column was glass, 1.6×20 cm (XK16X20, Pharmacia, Uppsala, SE). It was packed and operated at room temperature. The column was packed with Bakerbond™ Wide Pore HI-Propyl, Cat. No. 7182-02 according to the manufacturer's recommendations to a bed volume of 12 mL. The column was operated on a dual pump bio-chromatography system equipped with a computer controlled gradient formation system (two pumps No. 222C with 0–30 mL/min heads; controller model 232D; Scientific Systems, State College, Pa.). It was equilibrated with start buffer (1.5 M ammonium sulfate, 20 mM sodium acetate, 1 µM leupeptin, pH 4.5) at 150 cm/hr. Prior to sample application to the column, the eluate pH was 4.3 to 4.7 and its conductivity was equal to that of the start buffer.

The sample was adjusted to pH 4.5 with acetic acid and brought to 1.5 M ammonium sulfate by addition of solid ammonium sulfate. A peristaltic pump was used for sample application. The column was loaded at 10 mg total protein per mL packed bed volume. The column was then eluted according to a programmed elution regime. The flow rate was 150 cm/hr throughout elution: linear gradient from start buffer to 60% elution buffer (20 mM sodium acetate, 1 µM leupeptin, pH 4.5) in 30 column volumes; hold for 10 column volumes; linear gradient from 60% elution buffer to 100% elution buffer in 2 column volumes. The eluate was collected by a fraction collector and the total protein and FSH immunological activity of these fractions was determined by the methods described above. FSH-containing fractions from HIC were pooled to form the final product which was then concentrated to about 7600 IU/mL and diafiltered with 50 mM ammonium bicarbonate. Diafiltration occurred in a stirred cell device (Model 8400, Amicon, Inc., Beverly, Mass.) equipped with a 10,000 Dalton ultrafiltration membrane (YM-10, Amicon, Inc., Beverly, Mass.).

Table 1 shows the data obtained from the DAC and HIC procedures used to produce a lot of affinity pure human FSH. Several lots have been produced using these same procedures with substantially similar results. The final product contained 0.39 IU of LH per mg total protein or 0.0038% and 0.0046 IU of TSH per mg of total protein or 0.054%. Analysis of the product by SDS-PAGE using the reducing system of Laemmlli (1970) stained with Coomassie Blue for protein revealed a single broad band at 21,000 to 23,000 Daltons. No other protein bands were detected. The single band is likely to contain both the alpha and beta subunits of FSH as these are known to co-migrate in this system (Keene, J. L., et al., 1989). The alpha and beta subunits of FSH can be resolved by use of isoelectric focusing.

TABLE 1

FSH Purification from human pituitary glands

| SAMPLE | FSH (IU) | LH (IU) | Protein (mg) | FSH Specific Immunological Activity (IU of FSH per mg total protein) | Purification (fold) | % Yield[1] |
|---|---|---|---|---|---|---|
| Pituitary Extract | 853,477 | 2,160,000 | 160,115 | 5.33 | NA | 100 |
| DAC starting sample | 852,480 | 1,868,130 | 3800 | 224.6 | 42.1 | 99.9 |
| DAC product | 837,670 | 29,960 | 78.6 | 10,657 | 47.5 | 98.3 |

TABLE 1-continued

FSH Purification from human pituitary glands

| SAMPLE | FSH (IU) | LH (IU) | Protein (mg) | FSH Specific Immuno- logical Activity (IU of FSH per mg total protein) | Pur- ifi- ca- tion (fold) | % Yield[1] |
|---|---|---|---|---|---|---|
| HIC starting sample | 641,162 | ND | 79 | 8116 | 0.76 | 76.5 |
| HIC product | 431,170 | 30 | 46.6 | 9253 | 1.14 | 67.0 |
| Final product | 318,697 | 26.5 | 45.1 | 7066 | 0.76 | 73.9 |
| Overall | | | | | | 37.3 |

[1]FSH immunological activity of product/FSH immunological activity of sample

EXAMPLE 2

Purification of FSH from Human Menopausal Gonadotropin

A sample of hMG was commercially obtained (Y.J. Bioproducts, Rancho Cordova, Calif.). It was provided at a potency of 177 IU of FSH per mg total protein as determined by enzyme immunoassay (EIA) and RIA. This sample was prepared for DAC on Orange 1 by reconstitution at 7.5 mg/mL in 1 mM Tris-acetate, 1 $\mu$M leupeptin, pH 9.5. To prepare the sample for binding to Orange 1, it was diafiltered with 5 to 10 volumes of the same buffer as used for reconstitution. Diafiltration occurred in a stirred cell device (Model 8400, Amicon, Inc., Beverly, Mass.) equipped with a 10,000 Dalton ultrafiltration membrane (YM-10, Amicon, Inc., Beverly, Mass.). The sample conductivity was 0.65 mS and the total protein concentration was 5.26 mg/mL. An aliquot of this sample was taken for FSH and LH activity determination by immunoassay as described in Example 1.

Chromatography was done in a glass column 1.6×20 cm (Amicon, Inc., Beverly, Mass.) which was packed with Mimetic Orange 1 (Prometic Biosciences, Inc., Burtonsville, Md.; Cat. No. A6XL 0030) to a bed volume of 11 mL. The column was equilibrated with start buffer (5 mM sodium acetate, 1 $\mu$M leupeptin, pH 4.0) at 3 mL/min for at least 8 column volumes. Prior to sample application to this column, the eluate pH was 3.8–4.3 and its conductivity was <1.3 mS. Chromatography occurred on a single pump bio-chromatography system equipped with a proportioning value allowing ternary gradient formation (Series III Digital Pump, Scientific Systems, State College, Pa.).

The sample was adjusted to pH 4.0 with acetic acid and was then applied to the column at 15 cm/hr. The sample was applied to the column using a 50 mL superloop (Pharmacia, Inc., Uppsala, SE) and an injection valve (Model 9125, Reodyne, Cotati, Calif.). The column was loaded at 14.4 mg total protein per mL packed bed volume. The column was then eluted according to a programmed elution regime. All elution was performed at 60 cm/hr: 10 column volumes with start buffer (5 mM sodium acetate, 1 $\mu$M leupeptin, pH 4.0); 10 column volumes with washout buffer (0.025 M NaH$_2$PO$_4$, 0.02% NaN$_3$, 1 $\mu$M leupeptin, pH 6.0); 10 column volume linear gradient from washout buffer to elution buffer (0.025 M NaH$_2$PO$_4$, 2.0 M NaCl, 1 $\mu$M leupeptin, 0.02% NaN$_3$, pH 6.0). The column eluate was collected by a fraction collector and the fractions were analyzed to determine total protein and FSH and LH immunological activity, as described in Example 1. The column was stored in 0.1 M NaCl/EtOH (75/25) (v/v).

In this example, the LH contamination in the FSH product of the DAC procedure was 3.45 IU of LH pre mg total protein or 0.03%. However, the FSH product immunological activity was 3250 IU of FSH per mg total protein and, by SDS-PAGE analysis, the FSH was estimated to be 95% pure. There was another band at about 27,000 Daltons in addition to the prominent FSH band at 22,000 to 24,000 Daltons. Hence, the FSH from the DAC procedure was further purified by HIC.

The FSH-containing fractions from the DAC run were eluted during the gradient to elution buffer as a rather broad peak following an earlier, sharper peak containing LH and non-hormone contaminants. This elution profile was nearly identical to that seen with DAC of human pituitary-derived FSH, except that the FSH-containing peak occurred earlier. The FSH sample was prepared for HIC by first pooling the FSH-containing fractions from the DAC run. The sample was then concentrated to 3800–7600 IU/mL FSH using a stirred cell ultrafiltration device (Model 8400, Amicon, Inc., Beverly, Mass.) equipped with a 10,000 Dalton cutoff membrane (YM-10, Amicon, Inc., Beverly, Mass.). The sample was diafiltered with 5 to 10 volumes of 50 mM ammonium bicarbonate at pH 8.1.

The chromatography column was glass, 5×50 mm (HR5/50, Pharmacia, Uppsala, SE). It was packed and operated at room temperature. The column was packed with Baker-bond™ Wide Pore HI-Propyl, Cat. No. 7182–02 according to the manufacturer's recommendations to a bed volume of 1.2 mL. The column was operated on a completely automated bio-chromatography system (Akta Explorer, Pharmacia, Uppsala, SE). It was equilibrated with start buffer (1.2 M ammonium sulfate, 20 mM sodium acetate, 1 $\mu$M leupeptin, pH 4.5) at 150 cm/hr. Prior to sample application to the column, the eluate pH was 4.3 to 4.7 and its conductivity was equal to that of the start buffer.

The sample was adjusted to pH 4.5 with acetic acid and brought to 1.2 M ammonium sulfate by addition of solid ammonium sulfate and then injected onto the column. The column was loaded at 0.5 mg total protein per mL packed bed volume. The column then was eluted according to a programmed elution regime. All elutions were performed at 150 cm/hr: linear gradient from start buffer to 70% elution buffer (20 mM sodium acetate, 1 $\mu$M leupeptin, pH 4.5) in 30 column volumes; hold for 10 column volumes; linear gradient from 70% elution buffer to 100% elution buffer in 2 column volumes. The eluate was collected by a fraction collector and the total protein and FSH immunological activity of these fractions was determined as described in Example 1.

Table 2 shows the data obtained from using the DAC and HIC procedures to produce a lot of affinity pure human urofollitropin (urinary-derived FSH, uFSH). The final product is contained 1.6 IU of LH per mg total protein or 0.015%; 0.001 IU of TSH per mg total protein or 0.017%, and 0.2 IU of hCG per mg total protein or 0.0015%. Analysis of the product by SDS-PAGE using the reducing system of Laemmlli (1970) stained with Coomassie Blue for protein revealed a single broad band at 22,000 to 24,000 Daltons. No other protein bands were detected. The single band is likely to contain both the alpha and beta subunits of FSH as these are known to co-migrate in this system (Keene, J. L., et al., 1989). The alpha and beta subunits of FSH can be resolved by use of isoelectric focusing.

TABLE 2

FSH Purification from human menopausal gonadotropin

| SAMPLE | FSH (IU) | LH (IU) | Protein (mg) | FSH Specific Immunological Activity (IU of FSH per mg total protein) | Purification (fold) | % Yield[2] |
|---|---|---|---|---|---|---|
| DAC Starting Sample | 22,346 | 285 | 126 | 177 | NA | 100 |
| DAC Product | 20,151 | 18.5 | 5.46 | 3691 | 20.9 | 90.2 |
| HIC Starting Sample | 21,099 | ND | 4.897 | 4309 | 1.17 | 104.7 |
| HIC Product | 10,805 | ND | 1.91 | 5657 | 1.31 | 51.2 |
| Final Product | 9005 | 3.68 | 1.43 | 6298 | 1.11 | 83.3 |
| Overall | | | | | | 40.3 |

[2]FSH immunological activity of product/FSH immunological activity of sample

The biological activity of the final product was 8287 IU of FSH per mg total protein using an assay comprising an in vitro cell line containing recombinant human FSH receptor and a cAMP responsive luciferase reporter gene (Albonese, et al., 1994). The ratio of biological to immunological activity was 1.32; this parameter ranged from 1.3 to 1.7 in different preparations. Similar ratios were obtained by identical purification of other samples of hMG with starting FSH immunological activities of 100 to 200 IU of FSH per mg total protein.

Less pure hMG may also be purified using the DAC and HIC procedures outlined above. However, hMG with immunological activities of 10 to 30 IU of FSH per mg total protein may also require purification by ion exchange chromatography. An hMG sample of 15 IU of FSH per mg total protein FSH was first subjected to DAC, according to the method described above, followed by CIX on Fractogel EMD SO$_3$-650M (EM Separations Technology, Gibbstown, N.J.) according to the procedure used to purify human FSH from pituitary extracts (Example 1). The resulting FSH was then purified to homogeneity by HIC, as described in Example 4.

EXAMPLE 3

Optimization of Dye Affinity Chromatography of FSH

The DAC procedure was optimized for human FSH purification. These studies were performed on a scaled-down version of the above-described chromatography systems used for purification of FSH from human pituitary glands or from hMG. Initial studies showed the importance of binding at low pH and low conductivity for the separation of pituitary LH and FSH. When binding to Orange 1 occurred at pH 6.0 (25 mM NaH$_2$PO$_4$), both LH and FSH bound tightly and separation of LH and FSH during elution was incomplete. It was further shown that LH loading was maximal at 8,000 IU per mL of Orange 1 resin (0.76 mg LH per mL of Orange 1 resin). Above this loading, LH spilled over into the non-adsorbed fractions. FSH loading was maximal at approximately 0.25 mg FSH per mL Orange 1 resin.

Studies using hMG as a sample also confirmed the importance of binding conditions for the separation of gonadotropins by DAC on Orange 1. As the binding pH was varied from pH 4.0, 5.0 and 5.5 in 5 mM sodium acetate, the FSH binding was 99.2%, 99.4% and 99.3% (Calculated from the amount applied minus the FSH recovered in the non-adsorbed fractions). However, the amount of hCG that bound to the column increased with the pH. Hence, optimum separation of hCG from FSH was obtained using pH 4.0 for binding, e.g., 5 mM sodium acetate at pH 4.0. Some hMG samples were found to be contaminated with hCG at about 2% (mass percent). The origin of this hCG contamination is unknown. Hence, for optimum separation of gonadotropins from human FSH derived from pituitary glands or post-menopausal urine, binding to Orange 1 in a low ionic strength (conductivity 0.5 to 1.0 mS) buffer at pH 4.0 is preferred.

Washout from Orange 1 is important for the removal of contaminates from the bound FSH and the purification achieved by the DAC procedure. A sample of hMG was used for experiments designed to determine optimum washout conditions. The effect of washout pH was first determined using washout buffers of pH 6, 7, 8 (25 mM NaH$_2$PO$_4$) and pH 9 (25 mM glycine). There was an increase in the amount of FSH recovered in the washout fractions as the pH of the washout buffer was increased. At pH 6, 1.9% of the applied FSH was recovered in the washout; at pH 7, 9.9% of the FSH was recovered in the washout; at pH 8, 11.6% of the applied FSH was recovered in the washout and at pH 9, 43.1% of the applied FSH was recovered in the washout. Hence, to optimize recovery and purification of FSH in DAC using Orange 1, the preferred washout buffer is at pH 6.0.

The effect of ionic strength on washout also was investigated. Phosphate buffer concentrations above 50 mM resulted in substantial washout of FSH together with contaminating proteins, e.g., at 120 mM, 30% of the bound FSH spilled into the washout. While 50 mM phosphate buffer at pH 6 can be used as a washout buffer, this resulted in spill over of approximately 8% of the applied FSH. Hence, the preferred washout buffer for the purification of FSH is 25 mM phosphate buffer at pH 6.0.

Parameters affecting the elution of FSH also were investigated using an hMG sample. While elution from Orange 1 occurs with an elution buffer having a pH above pH 8, we have focused on the use of sodium chloride gradients at pH 6 for the ease of use of these procedures in a production environment. A study of the effects of changing the gradient endpoint from 2 M to 1 M to 0.8 M to 0.6 M NaCl showed that a 10 column-volume gradient from 0 M NaCl to 0.6 M NaCl was sufficient to completely elute the FSH bound to Orange 1.

Loading of Orange 1 was found to be dependent on the specific immunological activity of the hMG sample. For hMG at 150–200 IU of FSH per mg total protein, optimum sample load is 5 to 10 mg total protein per mL packed bed volume of Orange 1 while hMG samples at 10 to 30 IU of FSH per mg total protein are applied at 40–50 mg total protein per mL packed bed volume.

After 10 use cycles the Orange 1 was regenerated by washing the column with the following: 3 column volumes of deionized water, 4 column volumes of 0.5 N NaOH, 4 column volumes of 5 mM EDTA-Na$_2$, 4 column volumes of 5.0 M urea, 4 column volumes of deionized water. The column was stored in 0.1 M NaCl/EtOH (75/25) (v/v).

In summary, the preferred method for DAC of hMG is as follows:
1. Sample buffer is 1 mM Tris, pH 7.0. Reconstitute the sample in this buffer and diafilter with 3 to 5 volumes across a 10,000 Dalton cutoff ultrafiltration membrane. Sample pH is adjusted to 4.0 using acetic acid just prior to chromatography.
2. A column is packed with Mimetic Orange 1 (Prometic Biosciences, Inc., Burtonsville, Md.; Cat. No. A6XL 0030) in a suitable high performance glass chromatography column. Use packing material of use cycle <N=10, where N is the number of regenerations. The column is equilibrated with 8 to 10 column volumes of start buffer (5 mM sodium acetate, pH 4.0).
3. The sample is applied to the column at 30 cm/hr to result in a loading of 5 to 50 mg total protein per mL packed bed volume, depending on the specific immunological activity of the sample.
4. Washout the column with 5 to 10 column volumes of start buffer at 60 cm/hr.
5. Washout the column with 10 to 15 column volumes of 25 mM $NaH_2PO_4$, pH 6.0 at 60 cm/hr.
6. Run a linear gradient from washout buffer to elution buffer (0.6 M NaCl, 25 mM $NaH_2PO_4$, pH 6.0) at 60 cm/hr in 10 column volumes.
7. The column is stored in 0.1 M NaCl/EtOH (75/25) (v/v).

EXAMPLE 4

Optimization of the Hydrophobic Interaction Chromatography of Urofollitropin As is shown in Table 2, the yield of FSH from the HIC procedure was 51% and the purification was 1.3-fold. While the product of this HIC procedure was homogeneous by SDS-PAGE and its contamination with LH was minimal, optimization was undertaken to improve the yield of this procedure. These studies were performed on a scaled-down version of the above-described chromatography systems used for purification of FSH from hMG. It was found that addition of an organic solvent to the elution buffer improved the yield of FSH from HIC on a C3 solid phase (Source 15 Iso, Pharmacia, Uppsala, SE). The yield of this hMG derived urofollitropin was 77.9% using a reverse salt gradient from 1.5 M $K_2HPO_4$, pH 8.5 to 20 mM Tris, pH 8.5. When the elution buffer contained 30% ethanol, the yield was quantitative.

A media screen experiment using resins of differing hydrophobicity investigated various alkyl substituents, including propyl, butyl, hexyl, octyl and decyl groups immobilized to cross-linked agarose (Prometic Biosciences, Inc., Burtonsville, Md.). In these runs, the start buffer was 1.5 M $K_2HPO_4$, pH 8.5, and the elution buffer was 20 mM $Na_2HPO_4$, 30% ethano pH 8.5. Each column was equilibrated with 5 column volumes start buffer and, following sample injection, the column was washed out with 10 volumes of start buffer. Elution occurred by running a 20-column volume linear gradient to elution buffer. The flow rate was 120 cm/hr throughout the run. The results showed quantitative recoveries of FSH from all five of the HIC resins. However, the greatest purification of residual hCG from FSH occurred with the decyl resin. Hence, the preferred method for the HIC of urofollitropin uses decyl-agarose 6XL resin (Prometic Biosciences, Inc., Burtonsville, Md.). The method was further optimized by using a flow rate of 90 cm/hr during sample application and washout. FSH was eluted at 60 cm/hr using a 10 column volume linear gradient from start to elution buffer. This is the preferred method for HIC of human FSH.

EXAMPLE 5

Purification of Bovine FSH

FSH was partially purified from an acidic bovine pituitary extract (pH 4.0) of 100 glands by use of CIX on Fractogel EMD SO3-650M (EM Separations Technology, Gibbstown, N.J.). The extract was bound to this resin at pH 4.5 in 0.2 M NaCl, 10 mM sodium acetate. Bovine FSH was eluted in 0.6 M NaCl, 8 mM sodium acetate, pH 4.5. This sample was adjusted to pH 9.5, and concentrated 20-fold using a stirred cell device (Model 8400; Amicon, Beverly, Mass.) equipped with a 10,000 Dalton ultrafiltration membrane (YM-10; Amicon, Beverly, Mass.). The sample was then diafiltered with 1 mM Tris-acetate, 1 $\mu$M leupeptin at pH 9.5 until the conductivity of the sample was less than 1 mS.

Chromatography occurred in a glass column 5×20 cm (XK 50/20; Pharmacia, Uppsala, SE) packed with Mimetic Orange 1 (Prometic Biosciences, Inc., Burtonsville, Md., Cat. No. A6XL 0030) to a bed volume of 130 mL. The column was equilibrated with start buffer (5 mM sodium acetate, 1 $\mu$M leupeptin, pH 4.0) at 60 cm/hr for at least 8 column volumes. The eluate pH was 3.8–4.3 and its conductivity was <1.3 mS. Chromatography occurred on a single pump bio-chromatography system (Series III Digital Pump; Scientific Systems, State College, Pa.).

The chromatography sample was adjusted to pH 4.0 with acetic acid. It was then applied to the column at 30 cm/hr, using a 50 mL superloop (Pharmacia, Uppsala, SE). The column was loaded at 5.5 mg total protein per mL packed bed volume and eluted at 60 cm/hr as follows: 10 column volumes with start buffer (5mM sodium acetate, 1 $\mu$M leupeptin, pH 4.0); 10 column volumes with washout buffer (0.025 M $NaH_2PO_4$, 0.02% $NaN_3$, 1 $\mu$M leupeptin, pH 6.0); 10 column volume linear gradient from washout buffer to elution buffer (0.025 M $NaH_2PO_4$, 2.0 M NaCl, 1 $\mu$M leupeptin, 0.02% $NaN_3$, pH 6.0). The column eluate was collected by a fraction collector and the fractions were analyzed to determine total protein as described in Example 1.

Bovine FSH was assayed using an enzyme-linked immunoabsorbant assay (ELISA) consisting of a beta subunit-specific bovine FSH monoclonal antibody (AgResearch, Upper Hutt, NZ) diluted 1/500 in 50 mM $NaHCO_3$ that was adsorbed to microtiter plates (Immulon 2; Dynex Technologies, Chantilly, Va.) by overnight incubation at 4° C. Non-adsorbed antibody was washed out with 0.15 M NaCl, 0.05% Tween 20 and non-specific binding was blocked by a 2 hour incubation at room temperature in 250 $\mu$l 1.0% BSA, 0.05% Tween 20, 50 mM Tris, pH 7.7. Ovine FSH (Endocrine Technologies, Newark, Calif.) standards prepared in the same buffer at 0.0, 1.25, 2.5, 5, 10, 5, 15 and 20 ng/mL, and chromatography fractions also diluted in the same buffer were then added to duplicate wells together with an alpha subunit-directed antibody, rabbit antibovine FSH (Biogenesis, Poole, UK) at 1/3000 dilution (100 $\mu$l of each) and incubated for 2 hours at room temperature. Wells were then washed four times with 0.15 M NaCl, 0.05% Tween 20. Secondary antibody was added: 100 $\mu$l of donkey anti-rabbit IgG-HRP (Jackson Immunoresearch Labs, West Grove, Pa.) at 1/1000 in 1.0% BSA, 0.05% Tween-20, 50 mM Tris, pH 7.7. This was allowed to incubate for 1 hour at room temperature. The wells were then washed as described above and incubated with tetra-methyl benzidine reagent (United Biotech, Mountain View, Calif.) for 15 minutes. The HRP color development reaction was stopped by adding 50 $\mu$l of 1 N $H_2SO_4$ and the absorbance was read at 450 nm in a microtiter plate reader.

This analysis showed that there were 10.7 mg FSH in the pituitary extract, at 0.05% purity by specific immunological activity. Purification by CIX yielded 7.1 mg FSH at 0.7% purity (14-fold purification). Purification by DAC on Orange 1 yielded 6.7 mg FSH at 22% purity representing a purification of 33-fold. Analysis of the product by SDS-PAGE using the reducing system of Laemmlli (1970) stained with Coomassie Blue for protein revealed two distinct bands at approximately 18,000 Daltons and 20,000 Daltons, possibly the alpha and beta subunits of bovine FSH, respectively.

EXAMPLE 6

Purification of Recombinant Human FSH

The starting sample was 250 mL of conditioned media from CHO cell culture of recombinant human FSH (Keene, et al.,1989). The sample was concentrated to about 50 mL using a hollow fiber ultrafiltration device equipped with a 10,000 Dalton cutoff membrane (AG Technologies, Needham, Mass.; Cat. No. UFP-10-E-4A) followed by diafiltration with 1 mM Tris, pH 8 until the sample conductivity was less than 1 mS. Chromatography occurred in a glass column 2.6×20 cm (XK 26/20; Pharmacia, Uppsala, SE) which was packed with Mimetic Orange 1 (Prometic Biosciences, Inc., Burtonsville, Md.; Cat. No. A6XL 0030) to a bed volume of 17.5 mL. The column was equilibrated with start buffer (5 mM sodium acetate, pH 4.0) at 60 cm/hr for at least 8 column volumes. The eluate pH was 3.8–4.3 and its conductivity was <1.3 mS. Chromatography occurred on an automated bio-chromatography system (Akta Explorer; Pharmacia, Uppsala, SE).

The chromatography sample was adjusted to pH 4.0 with acetic acid and then applied to the column at 30 cm/hr. The column was loaded at 33.2 mg total protein per mL packed bed volume. The column was eluted at 60 cn/hr as follows: 5 column volumes start buffer (5 mM sodium acetate, pH 4.0); 15 column volumes washout buffer (0.025 M $NaH_2PO_4$, pH 6.0); 10 column volume linear gradient from washout to elution buffer (0.025 M $NaH_2PO_4$, 0.6 M NaCl, pH 6.0) followed by a 5 column-volume hold at these conditions. The column eluate was collected by a fraction collector and the fractions analyzed to determine total protein and human FSH as described in Example 1.

The starting sample contained 6.6 IU FSH at 11.4 mIU of FSH per mg total protein specific immunological activity. The product FSH was eluted as a single peak during gradient elution to 0.6 M NaCl: a total of 12.1 IU FSH was recovered at 8.67 IU of FSH per mg total protein specific immunological activity. Greater than quantitative recovery may be due to co-elution of FSH previously bound to the packing material. The eluted FSH was purified 760-fold, fold, suggesting substantial purification of recombinant human FSH by the method. Higher purification than observed with other samples may relate to the lower starting purity of the sample and clearance of serum proteins by the DAC procedure.

EXAMPLE 7

Purification of FSH Secreted from Cultured Human Gonadotropes

Human fetal pituitary glands (Anatomical Gift Foundation, White Oak, Ga.) stored in culture media at 4° C., were processed within 12 hours of extraction using aseptic methods as follows: 1) Glands were quickly immersed in 70% ethanol and rinsed with media (DME/F12 with phenol red, Atlanta Biologicals, Norcross, Ga.). 2) Tissue was minced thoroughly with small scalpels. 3) Tissue was collected in a small (1–2 mL) volume of media. 4) Collagenase (Sigma Chemical Co., St. Louis, Mo.) was added to 1 mg/mL. The mixture was incubated at 37° C. with shaking at 250 rpm, for a total of 45 to 60 minutes. The mixture was triturated every 15 minutes. 5) The mixture was brought to 10 mL with media, the pellet was resuspended and then centrifuged for 5 minutes at 150×g. 6) This step was repeated. A cell count was taken using a hemacytometer. 7) Cells were resuspended in serum-free media, Opti-MEM (Life Technologies, Gaithersburg, Md.) supplemented with insulin (5 $\mu$g/mL), transferrin (5 $\mu$g/mL), estradiol (1 nM) and long IGF-I (5 ng/mL) at about $5 \times 10^4$ cells/mL. 8) Cells were plated in 24 well culture plates (VWR Scientific, Inc., Dallas, Tex.) previously coated with Matrigel (Collaborative Biomedical Products, Bedford, Mass.) according to the manufacturer's recommended method. Cultures were maintained in a humidified, 5% $CO_2$ incubator at 37° C. Plated cells were visualized with an inverted, phase contrast microscope.

The status of hormone-producing cells was monitored by determining secretion of pituitary hormones into culture media. An automated chemiluminescent-based immunoanalyzer ACS:180™ (Chiron Diagnostics, Inc., Norwood, Mass.) was used to determine FSH, LH, prolactin, and TSH content of the media. While all hormones could be detected initially in these cultures, LH in particular showed a rapid decline and some cultures showed low, but sustained secretion of prolactin and TSH for periods up to 10 weeks. However, FSH secretion was maintained by cultures of several different pituitary glands as shown in Table 3.

TABLE 3

Secretion of human FSH by primary cultured fetal pituitary cells*

| Week | Pituitary 1 FSH (mIU/mL) | Pituitary 2 FSH (mIU/mL) | Pituitary 3 FSH (mIU/mL) |
|---|---|---|---|
| 1 | 26 | 13 | 12 |
| 2 | 67 | 29 | 26 |
| 3 | 80 | 120 | 37 |
| 4 | 105 | 77 | 11 |
| 5 | 92 | 37 | 16 |
| 6 | 18 | 64 | 88 |
| 8 | 25 | 99 | 13 |
| 10 | 25 | 89 | NA |
| 11 | 14 | NA | NA |

*Corrected for reactivity of media itself, about 8 mIU/mL.

The media conditioned by exposure to primary cultured human pituitary cells was collected and stored frozen. A conditioned media sample (210 mL) was prepared for chromatography by concentration to about 30 mL using a stirred cell device (Model 8400; Amicon, Beverly, Mass.) equipped with a 10,000 Dalton ultrafiltration membrane (YM-10; Amicon, Beverly, Mass.). The sample then was diafiltered with 1 mM Tris-acetate, pH 7.0 until the conductivity of the sample was less than 1 mS.

The sample was chromatographed in a glass column 1.6×20 cm (XK 16/20; Pharmacia, Uppsala, SE) which was packed with Mimetic Orange 1 (Prometic Biosciences, Inc., Burtonsville, Md.; Cat. No. A6XL 0030) to a bed volume of 1.6 mL. The column was equilibrated with at least 8 column volumes start buffer (5 mM sodium acetate, pH 4.0) at 60 cm/hr. The eluate pH was 3.8–4.3 and its conductivity was <1.3 mS. Chromatography occurred on an automated bio-chromatography system (Akta Explorer; Pharmacia, Uppsala, SE).

The chromatography sample was adjusted to pH 4.0 with acetic acid and then applied to the column at 30 cm/hr. The column was loaded at 51 mg total protein per mL packed bed volume. Elution occurred at 60 cm/hr as follows: 5 column volumes with start buffer (5 mM sodium acetate, pH 4.0); 15 column volumes with washout buffer (0.025 M $NaH_2PO_4$, pH 6.0); 10 column volume linear gradient from washout buffer to elution buffer (0.025 M $NaH_2PO_4$, 0.6 M NaCl, pH 6.0). The column eluate was collected by a fraction collector and the fractions were analyzed to determine total protein and human FSH as described in Example 1.

A total of 1200 mIUs FSH was recovered with a specific immunological activity of 510 mIUs FSH per mg total protein. This represented a 10.7-fold purification of the starting sample and a recovery of 31% of the applied FSH immunoactivity.

EXAMPLE 8

Additional Methods for the Purification of FSH from Human Menopausal Gonadotropin.

FSH is purified from hMG (FSH specific immunological activity about 15 IU of FSH per mg total protein; Hong Kong Institute for Biotechnology, Hong Kong, China) by reconstitution of hMG in 1 mM Tris, pH 7.0 at 40 mg/mL by weight. The $A_{280}$ is determined and the sample is concentrated to about 80% of its original volume in a hollow fiber ultrafiltration device (M12, ProFlux™; Amicon, Inc., Beverly, Mass.) equipped with a 10,000 Dalton-cutoff membrane (S10Y10, Amicon, Inc., Beverly, Mass.). Concentration occurs at 3 L/min with 15 PSI back pressure applied to the hollow fiber cartridge. The sample is then diafiltered with 1 mM Tris at pH 7.0 until the conductivity of the sample is less than 1 mS. The recovered sample is then centrifuged at 6300×g for 15 minutes and the volume of the supernatant is measured. Its conductivity and $A_{280}$ is determined and a small aliquot is removed for immunoassay.

Chromatography occurs in a glass column 2.6×20 cm (XK 26/20; Pharmacia, Uppsala, SE), packed with Mimetic Orange 1 (Prometic Biosciences, Inc., Burtonsville, Md., Burtonsville, Md.; Cat. No. A6XL 0030) to a bed volume of 20.0 ML. The column is equilibrated with start buffer (5 mM sodium acetate, pH 4.0) at 60 cm/hr for at least 8 column volumes. The eluate pH is 3.8–4.3 and its conductivity is <1.3 mS. Chromatography occurs on an automated bio-chromatography system (Akta Explorer; Pharmacia, Uppsala, SE).

The chromatography sample is adjusted to pH 4.0 with acetic acid just prior to applying to the column at 30 cm/hr. The column is loaded at 40–50 mg total protein per mL packed bed volume. The column is eluted at 60 cm/hr as follows: 5 column volumes start buffer (5 mM sodium acetate, pH 4.0); 15 column volumes washout buffer (0.025 M $NaH_2PO_4$, pH 6.0); step-wise increase in ionic strength to elute bound FSH with 3 column volumes of elution buffer (0.6 M NaCl, 0.025 M $NaH_2PO_4$, pH 6.0) at 60 cm/hr. Depending on the nature of the starting sample, an additional wash with 3 column volumes of 0.5 M NaCl, 0.025 M $NaH_2PO_4$, pH 6.0 at 60 cm/hr is used before the FSH elution. Elution with 3 column volumes of 0.05 M $Na_2HPO_4$ at pH 9.0 at 60 cm/hr is an alternative method of releasing FSH bound to the column. The column eluate is collected by a fraction collector and the fractions analyzed to determine total protein and human FSH immunological activity as described in Example 1.

Purified FSH resulting from DAC on Orange 1 can be further purified by HIC. The FSH sample is adjusted to pH 7.0 and diafiltered with 1 mM Tris, pH 7 until its conductivity is less than 12 mS using a stirred cell device (Model 8400; Amicon, Beverly, Mass.) equipped with a 10,000 Dalton ultrafiltration membrane (YM-10; Amicon, Beverly, Mass.). The sample volume, conductivity and $A_{280}$ are determined.

Chromatography occurs in a glass column 1.6×20 cm (XK 16/20; Pharmacia, Uppsala, SE) packed with $EMD-SO_3-$650M (EM Separations Technology, Gibbstown, N.J.) to a bed volume of 10 mL. The column is equilibrated with start buffer (0.1 M NaCl, 8 mM sodium acetate, pH 4.5) at 90 cm/hr for at least 10 column volumes. The eluate pH is 4.3–4.7 and its conductivity is equal to that of the start buffer. Chromatography occurs on a single pump bio-chromatography system (Series III Digital Pump; Scientific Systems, State College, Pa.).

The sample is applied to the column at 60 cm/hr using a superloop (Pharmacia, Uppsala, SE) at a loading of about 20 mg total protein per mL packed bed volume. The column is eluted as follows: 20 column volumes start buffer (0.1 M NaCl, 8 mM sodium acetate, pH 4.5) at 90 cm/hr; 10 column volumes washout buffer (80 mM $NaH_2PO$, pH 5.5) at 60 cm/hr; 10 column volumes elution buffer (0.8 M NaCl, 8 mM sodium acetate, pH 5.5) at 60 cm/hr. Fractions are collected during the run and analyzed for total protein and FSH immunological activity as described in Example 1.

The bound FSH is eluted by the step to 0.8 M NaCl. These fractions are pooled and prepared for chromatography by concentration to about 20% of the original volume by using a stirred cell device (Model 8400; Amicon, Beverly, Mass.) equipped with a 10,000 Dalton ultrafiltration membrane (YM-10; Amicon, Beverly, Mass.). The sample volume, conductivity and $A_{280}$ are determined.

Chromatography occurs in a glass column 1.6×20 cm (XK 16/20; Pharmacia, Uppsala, SE) packed with Prometic Decyl Agarose (Prometic BioSciences, Inc.; Burtonsville, Md.) to a bed volume of 10 mL. The column is equilibrated with start buffer (1.4 M potassium phosphate buffer, pH 8.5) at 90 cm/hr for at least 5 column volumes. The eluate pH is 8.3–8.7 and its conductivity is equal to start buffer. Chromatography occurs on a single pump bio-chromatography system (Series III Digital Pump; Scientific Systems, State College, Pa.).

The sample is brought to 1.4 M potassium phosphate by addition of solid potassium phosphate and applied to the column at 90 cm/hr using a superloop (Pharmacia, Uppsala, SE). The column is eluted as follows: 10 column volumes start buffer (1.4 M potassium phosphate, pH 8.5) at 90 cm/hr; a 10 column volume linear reverse salt gradient from start buffer to 50% elution buffer (20 mM $NaH_2PO_4$, 30% EtOH, pH 8.5) at 60 cm/hr followed by a hold at these conditions for 10 column volumes; step to 100% elution buffer at 60 cm/hr and hold for 10 column volumes. Fractions are collected during the run and analyzed for total protein and FSH immunological activity as described in Example 1 and for biological activity as described in Example 2. Highly purified FSH is released from the column during the reverse salt gradient.

FSH produced by the above method is >95% pure, has a specific biological activity of 7000 IU of FSH per mg total protein, a biological/immunological activity ratio of 1.8, LH contamination of <0.05%, hCG contamination of <0.05%, and TSH contamination of <0.05%. It appears as a single band by SDS-PAGE analysis using the reducing system of Laemmlli (1970) stained with Coomassie Blue for protein.

While the exemplary preferred embodiments of the present invention are described herein with particularity, those having ordinary skill in the art will recognize various changes, modifications, additions, and applications other than those specifically described herein, and may adapt the preferred embodiments and methods without departing from the spirit of the invention.

All documents cited herein are incorporated herein by reference.

Documents cited

1. Albonese, C., Christin-Maitre, S., Sluss, P. M., Crowley, W. F., and Jameson, J. L., Development of a bioassay for FSH using a recombinant human FSH receptor and a cAMP responsive luciferase reporter gene. Molec. Cell. Endocrin. 101:211–219, 1994.
2. Boland, J., Carey, G., Krodel, E., and Kwiatkowski, M., The CIBA Corning ACS:180™ benchtop immunoassay analyzer. Clin. Chem 36:1598–1602, 1990.
Bonde, M., Frokier, H., and Pepper, D. S., Selection of monoclonal antibodies for immunoaffinity chromatography: model studies with antibodies against soy bean trypsin inhibitor. J. Biochem. Biophys. Meth. 23:73–82, 1991.
4. Chappel, S. C., Ulloa-Aguirre, A., and Coutifaris, C., Biosynthesis and secretion of follicle-stimulating hormone. Endoc. Revs. 4:179–211, 1983.
5. Donini, P., Puzzuoli, D., D'Alessio, I., Lunenfeld, B., Eshkol, A. and Parlow, A. F., Purification and separation of follicle stimulating hormone (FSH) and luteinizing hormone (LH) from human postmenopausal gonadotropin (HMG). II. Preparation of biological apparently pure FSH by selective binding of LH with an anti-HCG serum and subsequent chromatography. Acta Endocrinol. 52:186–198, 1966.
6. Fiore, M. Mitchell, J. et al., The Abbott Imx™ automated benchtop immunochemistry analyzer system. Clin. Chem. 34:1726–1732, 1988.
7. Garg, N., Galaev, I. Y., and Mattiasson, B., Dye-affinity techniques for bioprocessing: recent developments. J. Mol. Recognit. 9:259–274, 1996.
8. Hartree, A. S., Separation and partial purification of protein hormones from human pituitary glands. Biochem. J. 100:754–761, 1966.
9. Hoffman, W. L. and O'Shannessy, D. J., Site-specific immobilisation of antibodies by their oligosaccharide moieties to new hydrazide derivatised solid supports. J. Immunol. Methods 112:113–120, 1988.
10. Jack, G. W., Blazek, R., James, K., Boyd, J. E., and Micklem, L. R., The automated production by immunoaffinity chromatography of the human pituitary glycoprotein hormones thyrotropin, follitropin and lutropin. J.Chem. Tech. Biotechnol. 39:45–58, 1987.
11. Jack, G. W., Immunoaffinity chromatography. Molec. Biotech. 1:59–86, 1994.
12. Keene, J. L., Matzuk, M. M., Otani, T., Fauser, B. C. J. M., Galway, A. B., Hsueh, A. J. W., and Boime, I., Expression of biologically active human follitropin in Chinese hamster ovary cells. J. Biol. Chem. 264:4769–4775, 1989.
13. Knight, P. G. Roles of inhibins, activins, and follistatin in the female reproductive system. Front. Neuroendocrinol. 17:476–509, 1996.
14. Laemmli, U. K. Cleavage of structural proteins during the assembly of the head of bacteriophage T4. Nature 227:680–685, 1970.
15. Lowe, C. R., Burton, S. J., Burton, N. P., Alderton, W. K., Pitts, J. M. and Thomas, J. A., Designer dyes: 'biomimetic' ligands for the purification of pharmaceutical proteins by affinity chromatography. Trends in Biotech. 10:442–448, 1992.
16. Moore, L. G., Ng-Chie, W., Lun, S., Lawrence, S. B., Young, W., McNatty, K. P., Follicle-stimulating hormone in the brushtail possum (Trichosurus vulpecula): purification, characterization and radioimmunassay. Gen. Comp. Endocrinol. 106:30–38, 1997.
17. Roos, P., Human Follicle-stimulating hormone. Acta Endocrinol. Suppl. 131, 9–93, 1968.
18. Szkudlinski, M. W., Teh, N. G., Grossman, M., Tropea, J. E., and Weintraub, B. D., Engineering human glycoprotein hormone superactive analogs. Nature Biotech. 14:1257–1263, 1996.
19. Japanese patent number 8,027,181. Purification of sialic acid-containing glycoprotein, used in foods, cosmetic, pharmaceuticals, etc. -comprises using chitosan porous beads.
20. Great Britain patent number 8,510,177. Isolating biologically active pituitary glycoprotein hormones by affinity chromatography, eluting with acidic buffer free of protein denaturant.
21. U.S. Pat. No. 5,128,453. Urinary follicle-stimulating hormone.
22. U.S. Pat. No. 5,338,835. Extended follicle stimulating subunit-has carboxy terminal peptide with residues of human chorionic gonadotropin beta subunit.

We claim:

1. A method for purification of follicle stimulating hormone (FSH) from an FSH-containing sample comprising the steps of:
   (a) applying the sample in a first buffer comprising a pH of less than about 7.5 to a dye affinity chromatography matrix comprising a dye ligand;
   (b) washing out contaminants from the chromatography matrix with a second buffer comprising a pH of less than about 9.0;
   (c) and eluting the FSH with a third buffer comprising less than about 0.8 M NaCl;
wherein the FSH is selected from a group consisting of human recombinant FSH, human FSH secreted from gonadotropes maintained in cell culture, genetically altered forms of human FSH, bovine FSH, equine FSH, porcine FSH, ovine FSH, canine FSH, rat FSH, feline FSH, mouse FSH, and monkey FSH.

2. The method of claim 1 wherein step (c) further comprises a step-wise increase in ionic strength.

3. The method of claim 1 wherein step (c) further comprises the use of a linear gradient.

4. The method of claim 1 wherein step (c) further comprises a step-wise increase in ionic strength and the FSH group further consists of human urinary FSH.

5. A method for purification of human pituitary FSH from an FSH-containing sample comprising the steps of:
   (a) applying the sample in a first buffer comprising a pH of less than about 7.5 to a dye affinity chromatography matrix comprising a dye ligand;
   (b) washing out contaminants from the chromatography matrix with a second buffer comprising a pH of less than about 9.0;
   (c) and eluting the FSH with a step-wise increase in ionic strength with a third buffer comprising less than about 1.0 M NaCl.

6. A method for purification of FSH from a sample comprising the steps of:
   (a) applying the sample in a first buffer comprising a pH of less than about 7.5 to a dye affinity chromatography matrix comprising a dye ligand;

(b) washing out contaminants from the chromatography matrix with a second buffer comprising a pH of less than about 9.0;

(c) and eluting the FSH with a third buffer comprising a pH of greater than or equal to about 8.0.

7. A method for purification of FSH from an FSH-containing sample comprising the steps of:

(a) applying the sample in a first buffer comprising a pH of less than about 7.5 to a dye affinity chromatography matrix comprising a dye ligand;

(b) washing out contaminants from the chromatography matrix with a second buffer comprising a pH of less than about 9.0;

(c) and eluting the FSH with a third buffer comprising a competitor of FSH binding to the dye ligand.

8. A method as in any one of claims 1–7 wherein the first buffer comprises a pH of less than about 6 and a conductivity of less than about 1 mS.

9. A method as in any one of claims 1–7 wherein the dye ligand is Orange 1, Orange 2, Yellow 2, or Green 1.

10. A method as in any one of claims 1–7 wherein the dye affinity chromatography matrix further comprises cross linked agarose triazine coupled to Orange 1.

11. A method as in any one of claims 1–7 wherein the second buffer comprises a salt concentration of about less than about 50 mM and a pH of less than about 8.

12. A method as in any one of claims 1–7 further comprising the step of purifying the FSH by chromatography on a hydrophobic solid phase.

* * * * *